US010071073B2

(12) United States Patent
Dudai et al.

(10) Patent No.: US 10,071,073 B2
(45) Date of Patent: Sep. 11, 2018

(54) **COMPOSITIONS CONTAINING AS THE ACTIVE INGREDIENT COMPONENTS FROM *SALVIA SCLAREA* SEED**

(71) Applicant: THE STATE OF ISRAEL, MINISTRY OF AGRICULTURE & RURAL DEVELOPMENT, AGRICULTURAL RESEARCH ORGANIZATION (ARO) (VOLCANI CENTER), Rishon Lezion (IL)

(72) Inventors: Nativ Dudai, Kfar Yeheskel (IL); Zohara Yaniv Bacharach, Tel Aviv (IL); Eli Putievsky, Tivon (IL); Diah Saadi, Bosmat Tivon (IL); Dan Schafferman, Ramat Gan (IL); David Chaimovitsh, Gan Ner (IL)

(73) Assignee: STATE OF ISRAEL, MINISTRY OF AGRICULTURE & RURAL DEVELOPMENT, AGRICULTURAL RESEARCH ORGANIZATION (ARO) (VOLCANI CENTER), Rishon Lezion (IL)

( * ) Notice: Subject to any disclaimer, the term of this patent is extended or adjusted under 35 U.S.C. 154(b) by 0 days.

(21) Appl. No.: 15/697,502

(22) Filed: Sep. 7, 2017

(65) Prior Publication Data

US 2017/0360738 A1 Dec. 21, 2017

Related U.S. Application Data

(60) Division of application No. 15/353,932, filed on Nov. 17, 2016, which is a continuation of application No. (Continued)

(30) Foreign Application Priority Data

Sep. 7, 2003 (IL) .......................................... 157785

(51) Int. Cl.
| | | |
|---|---|---|
| *A61K 31/202* | (2006.01) |
| *A23L 7/135* | (2016.01) |
| *A61Q 19/08* | (2006.01) |
| *A21D 2/36* | (2006.01) |
| *A23D 9/00* | (2006.01) |
| *A61K 36/537* | (2006.01) |

(Continued)

(52) U.S. Cl.
CPC ............ *A61K 31/202* (2013.01); *A21D 2/266* (2013.01); *A21D 2/36* (2013.01); *A23D 7/001* (2013.01); *A23D 7/003* (2013.01); *A23D 7/0053* (2013.01); *A23D 7/0056* (2013.01); *A23D 9/00* (2013.01); *A23K 20/10* (2016.05); *A23K 20/158* (2016.05); *A23K 40/20* (2016.05); *A23K 50/75* (2016.05); *A23K 50/80* (2016.05); *A23L 2/39* (2013.01); *A23L 7/109* (2016.08); *A23L 7/126* (2016.08); *A23L 7/135* (2016.08); *A23L 7/198* (2016.08); *A23L 17/30* (2016.08); *A23L 17/35* (2016.08); *A23L 23/00* (2016.08); *A23L 27/60* (2016.08); *A23L 29/206* (2016.08); *A23L 33/105* (2016.08); *A23L 33/115* (2016.08); *A61K 8/361* (2013.01); *A61K 8/97* (2013.01); *A61K 36/537* (2013.01); *A61Q 19/00* (2013.01); *A61Q 19/08* (2013.01); *C11B 1/06* (2013.01); *C11B 9/02* (2013.01); *C11B 9/025* (2013.01); *A23V 2002/00* (2013.01); *A61K 2236/15* (2013.01); *A61K 2236/30* (2013.01)

(58) Field of Classification Search
CPC .......... A21D 2/266; A21D 2/36; A21D 7/001; A21D 7/003; A21D 7/0056; A21D 9/00; A23K 20/10; A23K 20/158; A23K 40/20; A23K 50/75; A23K 50/80; A23L 2/39; A23L 7/109; A23L 7/126; A23L 7/135; A23L 7/198; A23L 17/30; A23L 17/35; A23L 23/00; A23L 27/60; A23L 29/206; A23L 33/115; A23V 2002/00; A61K 8/361; A61K 8/97; A61K 31/202; A61K 36/537; A61K 2236/15; A61K 2236/30; A61Q 19/00; A61Q 19/08; C11B 1/06; C11B 9/02; C11B 9/025

See application file for complete search history.

(56) References Cited

U.S. PATENT DOCUMENTS

| 5,002,767 A | 3/1991 | Masse |
| 5,908,771 A | 6/1999 | Liu et al. |

(Continued)

FOREIGN PATENT DOCUMENTS

| WO | 99/62356 A1 | 12/1999 |
| WO | 99/62359 A1 | 12/1999 |

(Continued)

OTHER PUBLICATIONS

Culpeper Culpeper's Complete Herbal, Evens, London, first pub. 1653, pp. 50-51 (Year: 1814).*
Potterton, Culpeper's Complete Herbal, Sterling Publishing Co. NY, NY, p. 46 (Year: 2007).*
Pash, http://lifehacker.com/5896806/which-alcoholic-drinks-are-healthiest, accessed Sep. 16, 2017 (Year: 2012).*
Susunweed.com, Clary Sage, 2000, Susunweed.com, http://www.susunweed.com/Article_ClarySage.htm, 5 pages.*

(Continued)

*Primary Examiner* — Trevor M Love
(74) *Attorney, Agent, or Firm* — Browdy and Neimark, PLLC

(57) ABSTRACT

The present invention concerns a food supplement comprising *Salvia sclarea* seeds, or flour, oil or pulp or extracts obtained from the seeds as well as finished food products comprising the food supplement. The present invention further concerns a nutraceutical or cosmetic preparation comprising as an active ingredient *Salvia sclarea* seeds, or flour, oil or pulp or extracts obtained from the seeds.

20 Claims, No Drawings

Related U.S. Application Data

13/946,402, filed on Jul. 19, 2013, now Pat. No. 9,532,964, which is a continuation-in-part of application No. 10/570,810, filed as application No. PCT/IL2004/000804 on Sep. 7, 2004, now abandoned.

(51) Int. Cl.

| | |
|---|---|
| A61K 8/97 | (2017.01) |
| C11B 1/06 | (2006.01) |
| C11B 9/02 | (2006.01) |
| A23K 20/158 | (2016.01) |
| A23K 50/75 | (2016.01) |
| A23K 20/10 | (2016.01) |
| A23K 50/80 | (2016.01) |
| A23L 33/105 | (2016.01) |
| A23L 33/115 | (2016.01) |
| A23L 29/206 | (2016.01) |
| A61Q 19/00 | (2006.01) |
| A61K 8/36 | (2006.01) |
| A23K 40/20 | (2016.01) |
| A23L 2/39 | (2006.01) |
| A23D 7/005 | (2006.01) |
| A23D 7/00 | (2006.01) |
| A21D 2/26 | (2006.01) |
| A23L 7/109 | (2016.01) |
| A23L 23/00 | (2016.01) |
| A23L 27/60 | (2016.01) |
| A23L 17/30 | (2016.01) |
| A23L 7/126 | (2016.01) |
| A23L 7/10 | (2016.01) |

(56) References Cited

U.S. PATENT DOCUMENTS

| | | | |
|---|---|---|---|
| 2002/0051840 A1* | 5/2002 | Andersen | C09K 15/06 426/541 |
| 2002/0146400 A1 | 10/2002 | Cincotta | |
| 2002/0168430 A1 | 11/2002 | Heeg et al. | |
| 2011/0183033 A1 | 7/2011 | Gillot | |
| 2011/0306666 A1 | 12/2011 | Minatelli et al. | |

FOREIGN PATENT DOCUMENTS

| | | |
|---|---|---|
| WO | 02072119 A1 | 9/2002 |
| WO | 2004022725 A1 | 3/2004 |

OTHER PUBLICATIONS

"Sage: The Genus *Salvia*," edited by S. E. Kintzios, Harwood Academic Publishers, Amsterdam, The Netherlands, 2000.

A.V. Patudin, I.U. Yusupova, and D.A. Voloshina "Fatty acid composition of seed oils of twelve *Salvia* species" Rastit. Resur; 12 (2) 1 pp. 272-279 (1976).

A. Mruk-Luczkiewicz; "Analysis of lipids occurring in seeds of genus *Salvia* 1" Herba Polonica, pp. 7-12 (1981).

V. Fer lay et al. "Fatty acid composition of seed oils from spontaneous species of the Mediterranean south-east area" Oleagineux, vol. 48, n°2, pp. 91-97 (1993).

N. Azean et al. "Fatty acid composition of seed oils of twelve *Salvia* species growing in Turkey" Chemistry of Natural Compounds, vol. 401 No. 3, pp. 218-221 (2004).

B.E. Phillipson, M.D., et al. "Reduction of plasma lipids, lipoproteins, and apoproteins by dietary fish oils in patients with hypertriglyceridemia" The New England Journal of Medicine, vol. 312, No. 191 pp. 1210-1216 (1985).

A. Leaf, et al. "Cardiovascular effects of n-3 fatty acids" The New England Journal of Medicine, vol. 318, No. 9, pp. 549-557 (1988).

D. Pitarokili, M. et al. "Composition and antifungal activity on soil-borne pathogens of the essential oil of *Salvia sclarea* from Greece" Journal of Agricultural and Food Chemistry, 50, pp. 6688-6691 (2002).

A. Medeiros, et al. "Biochemical and functional characterization of the Tn-specific lectin from *Salvia sclarea* seeds" European Journal of Biochemistry, 2671 pp. 1434-1440 (2000).

Gusakova, S.D. et al. "The Oil of the Seeds of *Salvia sclarea*" Khimiya Prirodnykh Soedinenii, vol. 4, No. 5 pp. 226, (1968).

Ferlay, V., et al. "Fatty acid composition of seed oils from wild species of the south-east Mediterranean" Oleagineux (Paris), vol. 48, No. 2, pp. 91-97. 26 ref.; Laboratoire de Chimie Organique Appliquee, x URA-CNRS, Faculte des Sciences et Techniques, 13397 Marseilles 13, France (1993).

Akhmedova, ER, et al. "Fatty acid composition of *Salvia sclarea* L seeds in Azerbeidzhan conditions." Doklady Akademii Nauk Azerbeidzhanskoi SSR, (1985), vol. 41, No. 1, pp. 69-73, 12 ref.; Secondary X Source: Referativnyi Zhurnal, 55 (Rastenievodstvo), 1985, 6.55.572 (1985).

Mruk-Luczkiewicz, A. "Analysis of lipids occurring in seeds of the genus *Salvia*." Herba Polonica, (1981 ), vol. 27, o. 1, pp. 7-12. 11 ref.; Instytut Technologii i Analizy Leku, Gdansk, Poland.

Savin, K., et al. "Study of fatty oils from some wild *Salvia* species." Arhiv za Farmaciju, (1984), 34(6), 293-8; Inst. Pharmacogn., Fac. Pharm., Belgrade, Yugoslavia.

Patudin, A.V., et al. "Content and quantitative composition of fatty oil in *Salvia* species seeds." Rastitel'nye Resursy, (1976), 12(2), 272-9; Mosk. S-kh. Akad. im. Timiryazeva, Moscow, USSR.

Gusakova, S.D., et al. "Oil from the seeds of *Salvia sclarea*." Khimiya Prirodnykh Soedinenii, (1968), 4(5), 315-16; Inst. Khim Rast. Veshchestv, Tashkent, USSR.

Makarov A, G.V., et al. "The investigation of the fatty oil from seeds of *Salvia sclarea*." Farmatsevtichnii Zhurnal (Kiev), (1963), 18(5), 16-19; Pharm. Inst. Kharkov.

Berlingozzi, S., et al. "The seed oils of *Salvia sclarea* and *Cosmos bipinnatus*." Bollettino Chimico Farmaceutico (1924), 63, 721-3.

Hirashima et al., "Encapsulated Specialty Oils Commercialized in Sao Paolo State, Brazil: Evaluation of Identity (Fatty Acid Profile) and Compliance of Fatty Acids and Vitamin E Contents with Nutrition Labeling," Food Sci Technol, Campinas 33:107-115 (2013).

Ixtaina et al., "Oxidative Stability of Chia (*Salvia hispanica* L.) Seed Oil: Effect of Antioxidants and Storage Conditions" J. Am Oil Chem Soc. 89:1077-1090 (2012).

Kozlowski et al., "Content and composition of oils in the diaspores of some species of medicinal plants from the family Libiatae", Herba Polonica, 1998, 44(3), pp. 161-164 and English Abstract from EICSearch.

Pubchem ID 5280934, "Linolenic Acid", accessed at https://pubchem.ncbi.nlm.nih.gov/compound/linolenic_acid#section=Top Jul. 3, 2017.

Pubchem ID 5280933, "gamma-Linolenic acid", accessed at https://pubchem.ncbi.nlm.nih.gov/compound/gamma-Linolenic_acid#section= Top, Jul. 3, 2017.

Albertson et al., Temptations, Simon and Schuster, pp. 76-77 and 294 (2002).

"Vial", Webster's 1913 Dictionary, www.webster-dictionary.org/definition/vial accessed Dec. 18, 2017.

Dabrowski et al., Composition and oidative stability of oil from *Salvia hispanica* L. seeds in relation to extraction method, Eur. J. Lipid Sci. Technol, 119:1600209 (2017).

Hagemann et al., Search for new industrial oils. XIV. Seed oils of labiatae, Lipids, 2:371-380 (1967).

SOFA Database Query "sclarea", providing fatty acid profile from Mruk-Luczkiewicz, sofa.mri.bund.de/Print_ResultDetail.php (1981).

* cited by examiner

COMPOSITIONS CONTAINING AS THE ACTIVE INGREDIENT COMPONENTS FROM *SALVIA SCLAREA* SEED

FIELD OF THE INVENTION

The present invention relates to food supplements and nutraceutical compositions for raising omega-3 levels in a subject.

BACKGROUND OF THE INVENTION

Current research in nutritional medicine indicates that the omega-3 fatty acids are essential components of the human diet. According to studies published in the British scientific journal Lancet, the observed low incidence of arteriosclerosis (fatty plaques development on the inner walls of the arteries which obstructs the blood flow), including coronary artery disease, chronic inflammatory disease and diabetes in Greenland Eskimos has been attributed to their traditional ethnic diet, consisting largely of meat from whale, seals, sea birds and fish. This diet is rich in fat and protein and low in carbohydrates, but it is extremely high in omega-3 polyunsaturated fatty acids, and especially rich in two omega-3 fatty acids: C22:6 (DHA) and C20:5 (EPA).

The most important omega-3 fatty acids are eicosapentaenoic acid (EPA), docosahexaenoic acid (DHA) and α-linolenic acid (ALA).

EPA is a direct source of an important substance called prostaglandin E3, which is directly responsible for making blood platelets less sticky, thus leading to an easier flow of blood. EPA is, therefore, involved in processes that inhibit blood clots whose presence threaten to obstruct the circulation; this mode of action is particularly important in the small capillaries of the heart.

DHA (docosahexaenoic acid) is an omega-3 fatty acid of almost equal importance to EPA. DHA comprises a significant amount of the tissues that make up the human brain as well as a large part of the retina of the eye.

Some of the most dramatic effects of increased intake of omega-3 fatty acids are the lowering of high blood pressure, reduction of serum triglyceride levels, and an increase in clotting time, all positive steps in the prevention of heart and blood vessel diseases. These beneficial effects of omega-3 fatty acids have been noted in both clinical trials and epidemiological studies. Omega-3 fatty acids were found to be extremely useful natural substances powerful enough to normalize the high cholesterol and triglyceride levels that are so extensive in modern populations.

Omega-3 fatty acids have also been shown to slow down or prevent cancerous tumor growth, prevent blood vessels from closing following vascular surgery, improve inflammatory diseases such as rheumatoid arthritis and relieve symptoms of psoriasis. In addition, omega-3 fatty acids are essential for proper vision and brain development in newborns.

The average western diet is low in fresh fish and sea food containing EPA and DHA. On the other hand, it is high in refined carbohydrates and saturated fats. This kind of diet can lead to a serious deficiency in the raw materials necessary for proper platelet function in the blood stream.

Linolenic acid is essential for ensuring healthy skin condition. Moreover, oils containing large amounts of omega-3 fatty acids were shown to be effective in preventing skin wrinkles. The ingestion of these oils markedly lowers the cholesterol content in the blood. α-Linolenic acid is a fatty acid found in some plants and can be converted by the body to EPA and DHA. Plant sources of α-linolenic acid include walnuts and walnut oil, flaxseed, rapeseed (used to make canola oil), soybeans, spinach, mustard greens and purslane.

α-Linolenic acid is produced in high quantities in several plants, mainly hemp (up to 23% α-linolenic acid is pressed from hempseed) and flax (50%). These oils normally have an "off" flavor and are seldom used as edible oils due to their bad taste and smell. Conventional food oils, such as rapeseed (canola) and soybean contain only small amounts of linolenic acid (11% and 7% respectively).

Researchers believe that a 1:1 ratio of omega-6 to omega-3 (omega-6 is found primarily in vegetable oils like corn, safflower or sunflower) may be important in preventing heart disease. It seems that omega-3's and omega-6's continually compete for control of important biochemical reactions in the body. When the portion of omega-6 is higher than that of omega-3, it can lead to an overproduction of hormone-like substances called prostaglandins and leukotrienes. Large amounts of these hormone-like substances can disrupt the immune system, initiate the build-up of plaque formations on artery walls, form blood clots and trigger dangerously irregular heart rhythms.

Currently, the ratio in the American diet is about 10 omega-6 to 1 omega-3, a ratio, some experts say, which is a dangerous oversupply of omega-6 fatty acids.

Dietary fish oils containing omega-3 fatty acids are increasingly recommended for their antithrombic and hypolipidemic (lowering blood lipid) effects (Phillipson, Rothrock, Connor, Harris and Illingworthm, *New England J. Med.*, 312:1210-16, 1985). Additional benefits of these oils are improvement of immunological function and fighting allergies (Leaf and Weber, *New England J. Med*, 318:549-557, 1988).

Omega-3 fatty acids from vegetable oils could provide all the above health benefits without any of the disadvantages of oil from animal source.

During ingestion of vegetable oil there is no uptake of cholesterol. Fish oils are a primary source of vitamins A and D. Most marine oils may supply potentially toxic amounts of vitamins A and D, by supplying a sufficient amount of EPA and DHA factors. Also, many vegetal omega-3 oils have a clean flavor have a good taste, at least as compared to bad tasting fish oils. Fish oils are usually contained in preservative-free gelatin capsules for convenience due to their bad taste and smell.

Aromatic (essential) oil derived from flowers of *Salvia sclarea* has been used up to date mainly as a perfume; this usage was known from the time of ancient Rome. Other secondary uses for this aromatic oil have been in the tobacco industry, and in herbal remedies to fight infection, and to regulate the digestive system. The natural habitat of the plant is in Syria, Italy and Southern France; and its growth requirements in terms of soil content are not particular. Currently, the former Soviet Union, North Africa, and Hungary are the largest producers of this oil, and prices range from S60-90 per liter of oil. The plant can withstand heat, and is found on mountainous terrain, where rainfall is not lower than 400 mm annually. The floral parts alone are used to produce the oil; inclusion of leaves will degrade the oil quality. Typically a single harvest of floral parts is performed. If harvest is performed prematurely, the oil will contain a large percentage of linoleic acetate, which lowers the quality of the oil.

No previous use has been made of the seeds of *Salvia sclarea*; previous uses, mainly as a perfume or essential oils, were from plant material derived from the flower.

WO 99/62356 concerns enhanced food for humans which has significantly higher omega-3 content by the use of oil obtained from *Salvia hispanica* seed. *Salvia hispanica* (Chia) is a summer annual belonging to the Labiate family. It originates in mountain regions extending from west central Mexico to northern Guatemala. Due to its endemic growth restriction to mountain regions of central and southern America and thus its natural habitat is very specific and growth requirements very particular, making seed grown from the plant not economical, the plants are not widespread and have not acquired wide commercial acceptance as a food source.

It should be emphasized that the presence of ALA omega-3 fatty acid in oil produced from the seeds of one or another plant does not in itself suffice to indicate that the plant will be a good and effective source for that fatty acid. The range of different parameters, such as commercial cultivability, climatic conditions, regulatory provisions, profile of the fatty acids, percentage of fatty acids, ratio of omega-3 to omega-6, stability, flavor, fragrance, color, acidity, moisture, toxins, allergens, presence of vitamins and antioxidants in the oil, as well as many other parameters, determine whether oil from a certain plant will be a good and effective source for ALA omega-3 fatty acid. Sometimes, one parameter alone, such as aftertaste (e.g. in flax oil or *Matthiola* oil), or overoxidation (in flax or *Salvia hispanica* oil), suffices to prevent use of the oil as an effective and stable source for ALA omega-3 fatty acid in a nutritional supplement. Obviously, such a plant source cannot be designated as a good and effective source, when a large number of drawbacks come together in terms of the parameters listed above.

SUMMARY OF THE INVENTION

It has now been discovered, surprisingly, that it is possible to produce from the seeds of the plant called clary sage, whose Latin name is *Salvia sclarea*, a plant oil which is rich in fatty acids of nutritional value, among them omega-3 fatty acids, and at the same time has no unpleasant taste or odor, that is free of toxins and does not oxidize easily upon contact with air. It is surprising that the oil from the seeds of *Salvia sclarea* have no sharp or unpleasant taste or odor because *Salvia sclarea* is known as a plant with a sharp odor, to the extent that it is used in industry in the preparation of essential oils, i.e., aromatic volatile oils which do not contain fatty acids and which are used in the fragrance and flavor industry and mainly in the perfume industry. One would have expected oil that is produced from seeds of this plant also to have a sharp taste and odor, and accordingly be unsuitable for incorporation into foods. It is further noted that the genus *Salvia* includes species that are known to contain different percentages of toxins (such as thujone), and therefore, in general, the health authorities place obstacles in the way of the approval of food supplements derived from *Salvia*, a fact which was likely to dissuade researchers from studying *Salvia* plants for the production of plant-based food supplements.

Furthermore, the discovery of the unique combination between the fatty acids in the plant (in addition to omega-3 fatty acid, the seeds of this plant are especially rich in oleic acid and other ingredients, and the oil produced contains an optimal ratio between omega-3 and omega-6) and the absence of toxins, including allergens or harmful substances, indicated that this plant could be very advantageously used for the production of a plant oil that could serve as a food supplement. In addition, it was discovered that oil produced from the seeds of *Salvia sclarea* is, surprisingly, more stable than would have been expected of an oil containing such a large quantity of ALA, and the advantageousness of this trait for industrial use in the food industry is apparent.

The present invention thus embodies numerous advantages, inter alia, in that it enables the production of a nutritional supplement containing omega-3 fatty acid which has a neutral fragrance and taste; is free of toxins, allergens or harmful substances such as heavy metals; tends to oxidize less; and producible in an agrotechnically efficient manner. Moreover, the chemical composition of a nutritional supplement according to the invention embodies a unique combination of fatty acids, minerals and other components, including oleic acid, calcium, fibers and amino acids, the composition and quantities of which could not have been foreseen, as also the optimal ratio between omega-3 and omega-6.

Seeds of selected lines of *Salvia sclarea* (Labiate) (also known as "clary sage") have an average oil content of 25-30%.

The inventors now disclose that the seed oil of this plant is a rich source of omega-3 α-linolenic acid (about 55%). The other components of this oil are two important fatty acids: oleic acid (C18:1), which is present in extremely high levels, and linoleic acid (C18:2). Both acids are unsaturated fatty acids and are essential in the human diet.

The present invention hereby discloses whole seeds, or oil, flour/powder, or pulp obtained from *Salvia sclarea* seeds, having all the health benefits of fish oil but none of its drawbacks (notably its bad taste, distinctive smell and quick rancidity). The oil or flour/powder has the additional above-mentioned benefits over other vegetable oils, and can be used for dietary supplements, as an active ingredient in pharmaceutical and cosmetic compositions, and for industrial uses.

Another important application of this vegetable oil is its use as a drying oil for painting and lubrication, due to its high content of polyunsaturated fatty acids, namely linolenic acid. Up to date, vegetative drying oil has been obtained from crops such as flax seeds and Tong trees. These crops do not lend themselves to mechanical harvesting and cleaning. *Salvia sclarea* seed oil is useful for industry, and is relatively easy to obtain.

The prior art discloses (WO 99/62356) oil, rich in omega-3, obtained from *Salvia hispanica*, which is an endemic plant restricted in its growth to the high mountain area of Central and South America. The present invention is based on the surprising finding that seeds obtained from another variant of *Salvia*, i.e. being *Salvia sclarea*, have better nutritional value than oil, or crushed seed, obtained from *Salvia hispanica* as will be shown in the detailed description part of the invention and have other significant properties that are superior thereto, including, taste, color and oxidative stability (i.e., long shelf life), in addition to the aforementioned ease of cultivation and harvesting.

The difference between *Salvia sclarea* and *Salvia hispanica* is expressed in additional aspects, such as the fact that the latter does not contain the combination of a high concentration of ALA together with a high concentration of oleic acid. Oleic acid (omega-9) is a monounsaturated fatty acid known to help in the prevention of coronary disease. Olive oil, for example, contains 55% to 85% of oleic acid, which is known to reduce the risk of arteriosclerosis, coronary disease and stroke. The oleic acid content in *Salvia sclarea* is almost four times higher than in *Salvia hispanica*. The ratio between omega-3 and omega-6 is greater in *Salvia sclarea*, as can be seen in Table 2, below. Furthermore, it is known that oil produced from *Salvia sclarea* contains sclareol, which is not found in *Salvia hispanica*. Likewise, the outstanding stability of the oil produced from the *sclarea* species does not exist in the *Salvia hispanica* species.

Furthermore, the present invention is based on the realization that not only the oil or crushed flour/powder of *Salvia sclarea* has higher nutritional value than the oil of *Salvia hispanica*, but also the growth of the plant of the *Salvia sclarea* variety, as compared to the *Salvia hispanica* variety is more economical. The *Saliva sclarea* plants can grow in any Mediterranean climate such as in the Middle East, in Europe (including Southern European countries such as Italy, Spain and Southern France as well as Northern and Eastern European countries such as Finland and Russia), North Africa, California and Australia; and its growth requirements in terms of soil content are not particular. The plant can withstand both heat and cold (even snow), and is found on mountainous terrain, where rainfall is even lower than 400 mm annually.

Beyond this, the seeds of *Salvia sclarea* possess numerous advantages compared to *Salvia hispanica*. Thus, for example:

The seeds of *Salvia hispanica* are generally likely to be dark, and thus unsuited to the color and texture of food products and supplements, in contrast to the seeds of *Salvia sclarea*, which have a light and uniform color. It has long been known that a dark color in the field of nutritional supplements is an undesirable trait. Sometimes, a dark color necessitates adding color lightening additives which could affect the traits of the active ingredient in the nutritional supplement. Therefore, a nutritional supplement whose original color is light possesses clear advantages.

The size and uniformity of the *Salvia sclarea* plants and their botanical traits enable more efficient cultivation.

*Salvia sclarea* is a perennial plant, whereas *Salvia hispanica* is an annual plant. Therefore, *Salvia sclarea* is more cost efficient (cheaper) to grow than *Salvia hispanica*, which suffers from an additional drawback, noted above, namely, the absence of phenotypic uniformity among individuals from the same species, e.g. variance in the size of the plants or in the time of ripening makes it difficult to harvest them by industrial means (combine harvesters).

The present invention is further based on the surprising finding that from among several species of different *Salvia*, the specific *Salvia sclarea* of the present invention was found to have an extremely high nutritional value and very long shelf life without rancidity.

Thus, the present invention concerns a composition for use as a food supplement comprising, as an active ingredient, a composition of matter selected from:
  a. *Salvia sclarea* seed;
  b. *Salvia sclarea* seed oil in an essentially pure form;
  c. extracts of *Salvia sclarea* seed;
  d. *Salvia sclarea* seed crushed or milled to form a flour or powder; and
  e. *Salvia sclarea* seed pulp.

The term "composition of matter" refers to several components (fatty acids, proteins, minerals, vitamins, dietary fibers) present as a mixture with specific ratios between the components.

The term "*Salvia sclarea* seed" refers to the whole seed, essentially in an unprocessed form as separated from the full plant.

The term "*Salvia sclarea* seed oil in an essentially pure form" refers to oil obtained from the seed, which is essentially free from other components. The oil may be obtained by various manners known to separate oil from plant-seeds without damaging their nutritional value.

Examples of manners for separating the oil include:
1) "cold press" achieved by crushing and pressing the seed, centrifugation of the pressed seed for collection of the oily fraction present in the supernatant, and optionally also purification by various means known in the art such as by using filters, collecting sediments, etc.;
2) By use of volatile hydrophobic solvents which initially dissolve the oil, and then are evaporated by application of heat and/or vacuum.
3) By use of liquid $CO_2$ or liquid nitrogen in extremely cold temperature ("super-critical extraction").

The term "*Salvia sclarea* seed, crushed or milled to form flour or powder" refers to crushing or milling of the seed to fine particles by any mechanical milling means known in the art in order to break the seed into smaller fragments such as crumbs of flour or particles of powder, and in those flour/powder forms, most of the nutrients are more available to the subject than in the whole seed.

The term "*Salvia sclarea* seed pulp" refers in fact also to "defatted *Salvia sclarea* seed flour". These two alternative terms refer to the seed after the oily fraction has been extracted therefrom, which pulp is especially rich in dietary fibers, minerals, vitamins and proteins and poor in fatty acids and calories.

The term "extract of *Salvia sclarea* seed" refers to any compound that is extracted from the seed by using aqueous or alcoholic, or other organic extracts. Typically, where the extracting liquid is water, mostly to fibers (dietary fibers).

By a preferred embodiment of the present invention, the food supplement consists essentially of:
  a. *Salvia sclarea* seed;
  b. *Salvia sclarea* seed oil in an essentially pure form;
  c. extract of *Salvia sclarea* seed;
  d. *Salvia sclarea* seed crushed or milled to form a flour or powder; and
  e. *Salvia sclarea* seed pulp.

Preferably, in accordance with a preferred embodiment of the invention, the composition of matter is *Salvia sclarea* oil or *Salvia sclarea* flour or powder.

By a more preferred embodiment of the invention the food supplement consists of:
  a. *Salvia sclarea* seed;
  b. *Salvia sclarea* seed oil in an essentially pure form;
  c. extract of *Salvia sclarea* seed;
  d. *Salvia sclarea* seed crushed or milled to form a flour or powder; and
  e. *Salvia sclarea* seed pulp.

By one embodiment, the food supplement further comprises a "carrier" suitable for consumption in food products. The carrier is chosen as a carrier known in the art for the specific type of composition of matter of the invention. For example, where the composition of matter of the invention is oil, the carrier may be other types of vegetable oils such as olive oil, rapeseed (canola) oil, corn oil, soy oil, wheat germ oil, coconut oil, peanut oil, sesame oil, palm oil, almond oil, nut, such as walnut, oil, etc. Where the composition of matter of the invention is powder or flour the "carrier" may be other types of flour/powder such as wheat, barley, corn, soy flour, oat flour, rice flour, tapioca, or rye flour.

By another possibility, the food supplement contains only one of the ingredients (a-e) above without any "carrier".

The present invention further concerns the use of an agent selected from a. *Salvia sclarea* seed;
b. *Salvia sclarea* seed oil in an essentially pure form;
c. extracts of *Salvia sclarea* seed;
d. *Salvia sclarea* seed crushed or milled to form a flour or powder; and
e. *Salvia sclarea* seed pulp for the preparation of a food supplement.

The food supplement above may be used for human or non-human consumption, preferably in order to increase the level of at least one omega-3 fatty acid in the subject. The non-human animal may be a farm animal, such as cattle (cow, goat, and sheep) or poultry (hens, ducks, turkeys), as well as fish grown in fish ponds, such as carp, bass, tilapia, trout, and pond-raised salmon.

The food supplement of the present invention is expected to raise the level of at least one omega-3 fatty acid in the meat of the non-human animal (cow, sheep, hens, fish), as well as to raise the level of at least one omega-3 fatty acid in the products of the animals, such as milk and eggs.

Thus, the present invention concerns a method for increasing at least one omega-3 fatty acid level in a subject, the method comprising administering to the subject an effective amount of the food supplement of the present invention. The subject may be as defined above and may be a human or non-human animal.

The term "effective amount" is an amount that increases the level of at least one omega-3 fatty acid in a statistically significant manner as compared to a control subject not fed with the food supplement of the present invention.

The increase in the level of omega-3 fatty acid in the animal may be adjusted in accordance with the type of subject and the desired level, but typically, for example, in egg yolks is an increase of 2- to 10-fold, preferably an increase of more than 4-fold, more preferably an increase of more than 6-fold.

By another aspect, the present invention concerns a method for increasing the level of at least one omega-3 fatty acid in egg yolks or in the meat of hens, the method comprising: administering to the hens an effective amount the food supplement of the present invention.

The term "effective amount" is as defined above.

The present invention further concerns a nutraceutical composition comprising a nutraceutically acceptable carrier and, as an active ingredient, a composition of matter selected from:
a. *Salvia sclarea* seed;
b. *Salvia sclarea* seed oil in an essentially pure form;
c. extracts of *Salvia sclarea* seed;
d. *Salvia sclarea* seed crushed or milled to form a flour or powder; and
e. *Salvia sclarea* seed pulp.

Preferably, the *Salvia* seed oil is prepared as disclosed above. More preferably, the nutraceutical composition consists essentially of a composition of matter selected from:
a. *Salvia sclarea* seed;
b. *Salvia sclarea* seed oil in an essentially pure form;
c. extracts of *Salvia sclarea* seed;
d. *Salvia sclarea* seed crushed or milled to form a flour or powder; and
e. *Salvia sclarea* seed pulp.

The term "nutraceutical composition" refers to any substance that is a food or a part of a food and provides medical or health benefits, including the prevention and treatment of disease or disorder.

The present invention further concerns a nutraceutical composition as defined above for the treatment of a disease or a disorder wherein a therapeutically beneficial effect may be evident by increasing the level of at least one omega-3 fatty acid.

The term "treatment . . . therapeutically beneficial effect" may refer to at least one of the following: decrease in at least one undesirable effect of the disease; slowing the deterioration caused by the disease; increase in the disease-free time period; or elimination of the disease altogether.

Typically, the disease or disorder is selected from: arthrosclerosis, coronary artery disease, chronic inflammatory disease such as rheumatoid arthritis and IBD, diabetes, cancer, prevention of blood vessels from closing after vascular surgery, relieving symptoms of psoriasis, skin wrinkles and depression and mood disorders. The disease may be any disease or condition which is known scientifically, or is discovered empirically, to benefit from the increase in the level of at least one omega-3 fatty acid in the subject.

The nutraceutical composition is typically taken orally, for example in the form of gel-capsules containing the oil, liquid formulation containing the oil, tablets containing the flour/powder as known in the art for preparing such compositions, but for several indications, such as psoriasis, and other dermal conditions (wrinkles, dry skin), the oil containing formulations (gel-caps, oil) may also be topically applied.

The present invention further concerns a cosmetic composition comprising a cosmetically acceptable carrier and, as an active ingredient, *Salvia sclarea* seed oil in an essentially pure form. Typically the cosmetic composition is for prevention of wrinkles of the skin and/or ensuring skin health.

The term "at least one omega-3 fatty acid" refers to any unsaturated fatty acid with its first double bond at the third carbon atom from the methyl-end. These fatty acids may be such as essential fatty acid, α-linolenic acid (ALA) as well as non essential fatty acids such as docosahexaenoic acid (DHA) and eicosapentaenoic acid (EPA).

The present invention further concerns a food product comprising the food supplement of the present invention. Examples of food products are as follows:
1. Food product comprising whole seeds of *Salvia sclarea*: granola-like cereals, granola-like snack bars, foodstuff for hens, cows, etc. After soaking in water the whole seeds may be used in whole breads, rolls, crackers, biscuits, etc.
2. For *Salvia sclarea* seeds, ground or milled to produce flour/powder: granola-like cereals, granola-like snack bars, and foodstuff for hens, cows, etc., whole breads, rolls, crackers, biscuits, pasta and other baked goods. The flour/powder may be used as thickener in gravy, soup, dips, dressings, and other prepared food that typically contains flour of some sort as a thickener.
3. For *Salvia sclarea* oil-formulated into oily pastes or dips (tahini, humus) and in oils and paste such as sesame oil or sesame paste, formulated into other vegetable oils or margarine and margarine-like spreads, salad dressings, fish oil, caviar-like products, etc.
4. The pulp (defatted seed flour), due to its high fiber content, is extremely suitable for the preparation of low calorie (diet) baked products (breads, rolls) and also for the preparation of diet drinks and shakes with high fiber, protein and mineral contents.

DETAILED DESCRIPTION OF THE INVENTION

*Salvia sclarea* has an average oil content of 25-30% in the seeds, with maximum levels of 60% omega-3-linolenic acid of the total fatty acids in the oil. *Salvia sclarea* lines were tested and evaluated as a potential new oil crop for dietary supplement for humans and animals, for use as an active ingredient in pharmaceutical and cosmetic compositions and mixtures and for industrial uses.

Omega-3 fatty acids from vegetable oils could provide all the above health and cosmetic benefits without any of the disadvantages of oil from animal sources.

Another important aspect of this vegetable oil is its quality as drying oil, for painting and lubrication, due to the high content of polyunsaturated fatty acids, namely linolenic acid. Up to date, vegetative drying oil is obtained from crops such as flax seeds and Tong trees. These crops do not lend themselves to mechanical harvesting and cleaning, as does *Salvia sclarea*.

The *Salvia sclarea* oil of the present invention has many advantages as compared to the previously known *Salvia hispanica* oil, as can be seen, for example, by the following comparative analyses in Tables 1-4:

Comparative Analysis *Salvia Sclarea* and *Salvia Hispanica*

TABLE 1

General contents

| Test per 100 g | *Salvia Sclarea* | *Salvia hispanica* |
|---|---|---|
| % moisture (g/100 gr) | 7.40 | 7.8 |
| % protein (g/100 gr) | 23.38 | 21.1 |
| % Fat (g/100 gr) | 26.20 | 32.3 |
| % Ash (g/100 gr) | 5.77 | 4.8 |
| % Crude Fiber(g/100 gr) | 20.60 | 21.1 |
| mg/100 g Calcium | 0.82-0.928 | 0.0680 |
| mg/100 g Phosphorus | 0.70-0.682 | 0.780 |
| mg/100 Potassium | 1.02-1.29 | 0.809 |
| g/100 g Dietary fibers | 17.80 | N/A |
| Saturated fat from total gr. fat | 2.50 | 3.35 |

As can be seen the *Salvia sclarea* seeds have a higher protein and dietary fiber content than *Salvia hispanica* seeds.

TABLE 2

Fatty acids contents

| Fatty Acid Profile | | Range (Salvia hispanica) | Range (Salvia Sclarea) |
|---|---|---|---|
| Myristic Acid | C14:0 | 0.1-0.1 | 0 |
| Palmitic Acid | C16:0 | 6.6-6.7 | 6.8-8.0 |
| Palmitoleic Acid | C16:1 | 0.1-0.1 | |
| Heptadecanoic Acid | C17:0 | 0.2-0.2 | |
| Heptadecenoic Acid | C17:1 | 0.1-0.1 | |
| Stearic Acid | C18:0 | 2.8-3.1 | 1.9-2.6 |
| Oleic Acid | C18:1 | 6.6-7.0 | 24.7-25.2 |
| Linoleic Acid | C18:2 | 18.6-18.9 | 12.1-14.8 |
| Linolenic Acid | C18:3(ω-3) | 58.2-59.1 | 49.9-56.0 |
| Linolenic Acid | C18:3(ω-6) | 0.0-0.1 | 0-0.2 |
| Arachidic Acid | C20:0 | 0.3-0.3 | |
| Gadoleic Acid | C20:1 | 0.1-0.1 | 0.6 |
| Eicosadienoic Acid | C20:2 | 0.1-0.1 | |
| Eicosatrienoic Acid | C20:3(ω-3) | 0.1-0.1 | |
| Behenic Acid | C22:0 | 0.1.0.1 | 0.1 |
| Docosatetraenoic Acid | C22:4 | 0.1-0.1 | |
| Lignoceric Acid | C24 | 0.2-0.2 | 0.1 |
| Total Fat | | 32.25% | 26.2% |

Ratio: $\frac{\text{omega 3}}{\text{omega 6}} = 3.12 \quad 3.95$

As can be seen, the omega 3:omega 6 ratio in *Salvia sclarea* seeds is higher than in *Salvia hispanica* seeds. Furthermore the oleic acid contents in *Salvia sclarea* seeds is significantly higher than in *Salvia hispanica* seeds.

TABLE 3 mineral profile

| In ( ) the recommended USRDA (mg) | *Salvia Sclarea*/ mg in 100 g seeds mg/kg | *Salvia hispanica* mg in 100 g seeds |
|---|---|---|
| Ag | <0.05 | |
| Al | 2.2 | N/A |
| Ag | <0.05 | <0.01 |
| B | 1.4 | N/A |
| Ba | 2.3 | N/A |
| Be | <0.01 | N/A |
| Ca (1000) | 928 | 679.8 |
| Cd | <0.01 | 0.018 |
| Co | <0.05 | 0.25 |
| Cr | 0.03 | 0.5 |
| Cu (2) | 1.9 | 1.7 |
| Fe | 8.4 | 9.9 |
| Hg | 0.07 | 0.01 |
| K (2500) | 1290 | 809 |
| Li | <0.09 | N/A |
| Mg (400) | 360 | 380 |
| Mn (4) | 4.3 | N/A |
| Mo | 0.06 | 0.25 |
| Na | 17.3 | 12.15 |
| Ni | <0.05 | 0.25 |
| p | 682 | 780 |
| Pb | <0.05 | <0.035 |
| s | 261 | 290 |
| Se (60 μg) | 0.06 (60 μg) | 1 |
| Sr | 2.2 | N/A |
| Ti | <0.03 | N/A |
| V | <0.05 | N/A |
| Zn | 5.6 | 4.4 |

As can be seen, the calcium, potassium and selenium content in the *Salvia sclarea* seeds are close to the RDA recommended amounts.

TABLE 4 amino acid contents

| | Compound | Total % Protein Sample | | | Ess. a.a. in 100 g *Salvia sclarea* seeds g/ukg |
|---|---|---|---|---|---|
| | | *Salvia Sclarea* | *Salvia hispanica* | USRDA g/day | |
| 1 | CysO3 | 1.06 | 1.82 | | |
| 2 | Aspartic | 9.65 | 9.47 | | |
| 3 | Met. sulf | 0.51 | 0.45 | Threon. 0.5 | |
| 4 | Threonine (Essential) | 3.99 | 4.25 | | 0.92 |
| 5 | Serine | 5.66 | 6.02 | | |
| 6 | Glutamic | 17.64 | 15.37 | | |
| 7 | Proline | 3.18 | 0.73 | | |
| 8 | Glycine | 6.16 | 5.23 | | |
| 9 | Alanine | 5.46 | 5.34 | Val. 0.8 | |
| 11 | Valine (Essential) | 5.05 | 6.32 | Meth. 1.1 | 1.16 |
| 12 | Methionine (Essential) | 0.51 | 0.45 | Isoleu. 0.7 | 0.19 |
| 13 | Isoleucine (Essential) | 3.79 | 3.98 | Leu. 1.1 | 0.87 |
| 14 | Leucine (Essential) | 7.78 | 7.30 | | 1.78 |
| 15 | Tyrosine | 4.19 | 3.41 | Phen. 1.1 | 1.45 |
| 16 | Phenylalanine (Essential) | 6.32 | 5.86 | N/A | |
| 17 | Histidine (Essential) | 2.63 | 3.19 | Lys. 0.8 | 0.60 |

TABLE 4-continued amino acid contents

|  | Compound | Total % Protein Sample | | USRDA g/day | Ess. a.a. in 100 g *Salvia sclarea* seeds g/ukg |
|---|---|---|---|---|---|
|  |  | *Salvia Sclarea* | *Salvia hispanica* | | |
| 18 | Lysine (Essential) | 3.69 | 5.50 | | 0.85 |
| 19 | Gamma aminobutyric acid | | | N/A | |
| 20 | Arginine (essential) | 10.71 | 11.03 | | 2.46 |
|  | Total: | ≈98% | ≈96% | | |

As can been seen, the amino acid contents in 100 g *Salvia sclarea* supplies 50-160% of the USRDA essential amino acid contents.

Example 1: Effect of *Salvia Sclarea* Seed-Products on Hens

An experiment was conducted to measure the toxicity of *Salvia sclarea* seed oil when administered as a dietary supplement to laying hens, and the resultant level of omega-3 fatty acid, as measured in the hens' body fat and in the resultant egg yolks.

11 kg of *Salvia sclarea* seeds were milled into crude flour, and mixed into standard hen feed at a concentration of 13.75% w/w. Concentrations of 15-17% of the *Salvia sclarea* flour would also have been appropriate, though they were not included in this experiment. The feed containing the *Salvia sclarea* flour was stored and used for the duration of the experiment, though typically hen feed is prepared immediately before use.

20 hens of the Yarkon variety were selected, having an age of 8.5 months. At termination of the experiment, the hens numbered 18; this is consistent with the standard mortality rate. The laying capacity was approximately 80-90% at the start of the experiment. The hens were fed once or twice daily by hand, so that each hen received approximately 120-130 gr. of feed, as estimated visually.

During the first two days, the hens showed classical symptoms seen when feed is changed. These symptoms disappeared thereafter.

No change was observed in the quantity of feed consumed by the hens, or in the degree of laying, though these values were not physically measured. The quality of the eggs, their size and breakage levels were not measured, but no change was visibly apparent.

At the start of the experiment (Day 1), 10 eggs were selected, refrigerated for 4 days, then their yolks were pooled and sent for chemical analysis. Yolks were refrigerated until analysis was performed. The yolk pool had a volume of 30 ml. The fatty acid content, the Total Fat, and the cholesterol levels were analyzed, and are presented in Table 5 below.

On Day 14 of the experiment, 10 additional eggs were selected and their pooled yolks were sent for analysis.

On Day 29, 10 yolks were once again pooled and analyzed, and 10 control yolks were likewise pooled and analyzed. The control yolks belong to hens raised in similar conditions; however, the control group did not receive *Salvia sclarea* flour supplement in the feed.

The experiment was discontinued at Day 34. Two hens were then selected, one being a hen in the experiment group, and one control hen. They were slaughtered and their body fat content was analyzed. Results are shown in Table 6 below.

In this experiment, the nutritional value of the *Salvia sclarea* seed itself was disregarded, though, for instance, feed containing *Salvia sclarea* flour has a higher oil content than standard feed.

Referring to Table 5, the percentage of linolenic acid present in the egg contents increased dramatically by 617%. The percentage of DHA increased as well, by 21%.

Referring to Table 6, the percentage of linolenic acid present in the body fat of hens that consumed *Salvia sclarea* flour rose dramatically, by 167%.

No toxicity was observed for *Salvia sclarea* seed flour.

These results demonstrate *Salvia sclarea* seeds are a viable source of omega-3 fatty acids and that consumption of *Salvia sclarea* seed flour results in a direct positive effect on the level of omega-3 fatty acids in the consumer. Dietary supplements containing *Salvia sclarea* seed flour or oil are thus nutritionally recommended and could aid in preventing or ameliorating arteriosclerosis and other conditions where high levels of omega-3 fatty acids have been found to be beneficial.

TABLE 5

Content of Eggs Produced by Hens after Consumption of *Salvia sclarea* Seed Flour

| | | % Fatty Acids In Oil | | |
|---|---|---|---|---|
| Fatty acid | Name | Control | Treated | % change |
| C14:0 | Myristic | 0.37 | 0.35 | — |
| C16:0 | Palmitic | 24.64 | 23.36 | −6 |
| C16:1 | Palmitolic | 3.18 | 3.55 | +5 |
| C18:0 | Stearic | 9.23 | 7.68 | −17 |
| C18:1 | Oleic | 42.28 | 43.26 | +2 |
| C18:2 | Linoleic | 15.78 | 15.51 | −2 |
| C18:3 | Linolenic | 0.57 | 4.09 | +617 |
| C20:5 | EPA | | | |
| C22:6 | DHA | 0.57 | 0.69 | +21 |
| Total fat in the egg(%) | | 20.9 | 23.0 | +10 |
| P/S ratio | | 0.47 | 0.69 | +21 |

TABLE 6

Content of Hen Body Fat after Consumption of *Salvia sclarea* Seed Flour

| | | % Fatty Acids in Oil | | |
|---|---|---|---|---|
| Fatty acid | Name | Control | Treated | % change |
| C14:0 | Myristic | 0.52 | 0.54 | +4 |
| C16:0 | Palmitic | 18.84 | 19.55 | +4 |
| C16:1 | Palmitolic | 3.71 | 4.70 | +27 |
| C18:0 | Stearic | 5.89 | 5.51 | −6 |
| C18:1 | Oleic | 37.95 | 40.88 | +8 |
| C18:2 | Linoleic | 29.75 | 23.57 | −21 |
| C18:3 | Linolenic | 1.44 | 3.85 | +167 |
| Total hen's fat (%) | | 55.3 | 37.6 | −32 |
| P/S ratio | | 1.23 | 1.07 | −7 |
| % S in Triglycerides | | 14.5 | 9.93 | −32 |

Based on the nutritional-chemical spectra of analysis, the general conclusions are that *Salvia sclarea* seeds can be regarded as nearly a nutritionally complete foodstuff.

Example 2: Calculations Concerning *Salvia Sclarea* as a Food Supplement for Human Consumption According to the analysis shown in tables 1-4 above, it is calculated that 100 grams of *Salvia sclarea* seeds per day will supply approximately 40% to 50% of the required proteins, including all the USRDA for essential Amino Acids (except a too low quantity of Methionine), approximately 40% of the daily recommendations for fats/oils (based on 2000 calories per day diet) with an excellent fatty acid profile that contains approximately 50% omega-3 ALA, 25% oleic acid, and 3.4 to 1 ratio of omega-3 to omega-6.

100 grams per day of *Salvia sclarea* seeds will also supply 75% of the recommended USA daily values for dietary fiber based on a 2000 calories diet (or 100% according the UK recommendations), 100% of the USRDA for most of the minerals (Ca, Mg, Cu, Se, Mn), 50% of the USRDA for Potassium (K) and Iron (Fe), 33% for Zinc (Zn) and Boron (B) 1.4 mg/100 g.

The *Salvia sclarea* seeds are also free of trans-fatty acids and gluten, and absorb approximately 8 times their weight in water, making them ideal for diet-low calorie foods, as fat replacement products and water binders.

Example 3: Production of *Salvia Sclarea* Flour/Powder

The *Salvia sclarea* seeds are ground into meal, blended with natural antioxidants to prevent oil oxidation (rancidity) and to prolong the shelf life of the product and then formulated as an ingredient into weight reducing, nutritionally balanced powdered drink mixes, bars and low-cal/low carbohydrate baked goods. As will be shown below, however, antioxidants are not absolutely necessary in light of the natural shelf life for the oil in the *Salvia sclarea* seeds,

Example 4: Production of Cereal Snacks and Pasta

The *Salvia sclarea* seeds are ground into meal, partially blended with whole seeds, formulated with other grain flours such as wheat, barley, soy or corn, together with natural binders and fibers, and then extruded by cooking extruders into flakes for breakfast cereals, and other shapes for snacks, then flavored, spiced, oil coated and baked (or fried) in oils blended with *Salvia sclarea* omega-3 enriched vegetable oils.

For production by "cooking extruders," a dry blend of *Salvia sclarea* meal and other ingredients are cooked together under high pressure, using a single or twin co-rotating screws inside a barrel with injection ports. Water and/or other liquids are injected into the barrel during the cooking and blending process. The extruded product is baked or air-dried, fried, and then flavored.

Formulations for cold extruded pasta products include usage of special natural colorings, dough improvers, spices, flavorings, fibers, etc., that render natural, omega-3 enriched pastas of various shapes and colors.

The extruded products can be used as such (without further processing) or mixed with other ingredients for production of health oriented dry or cooked meals, breakfast cereals, granola mixes, etc. Using state-of-the art formulations for cold-extrusion systems omega-3 enriched pasta is obtained in various shapes and colors (using natural colors also with antioxidant activities).

Example 5: Production of Low-Calorie Baked Goods

*Salvia sclarea* whole seeds are pretreated by soaking in water or other suitable liquids or marinades, and then formulated into low-calorie, nutritionally enhanced baked goods. For example, in one embodiment a 250 calorie per 100 gram standard bread has its energy reduced by 40% to a 150 calorie per 100 gram diet bread. Similarly, a substantial reduction in calories applies to buns and rolls, biscuits, bagels, etc. These low-calorie baked goods, which are also omega 3 enriched, are suitable also for fast food chains (buns for hotdogs or hamburgers), sandwiches, etc.

The *Salvia sclarea* seeds are marinated in buffered, flavored and naturally colored solutions for varying lengths of time as desired. Temperature and pH are controlled.

The marinated seeds and also *Salvia sclarea* flour/powder are mixed into bread dough and other bakery products and baked accordingly. The marinated seeds will render products containing them low calorie products and also low-carbohydrates (low-carb.) since the bound water marinade will react with the *Salvia sclarea* fibers to form a soft jelly-type mixture.

Example 6: Production of Oil

*Salvia sclarea* seed oil is extracted from seeds, blended with other oils, vegetable proteins, water, and natural emulsifying and stabilizing ingredients and then homogenized by a homogenizer and formed into a butter/margarine-like flavored spread, free of trans fatty acids, very low in saturated fats, and high in omega-3 and oleic fatty acids.

*Salvia sclarea* seed oil is extracted from *Salvia* seeds by a multi-stage press-extractor. Prior to extraction the seeds are lightly heated and wetted for maximum yields.

The excess water is then removed by a decanting centrifuge. The omega-3 rich and oleic acid rich oil is collected, blended with natural oxidants, if desired, and bottled as such or blended with other oils (see also Example 8), bottled or blended with other ingredients (emulsifiers, stabilizers, water, etc.) and then homogenized under vacuum to produce high omega-3 and oleic acid butter-like spreads, vegetarian mayonnaise, etc.

Example 7: Production of Paste

*Salvia sclarea* seeds, rich in proteins, omega-3 oil and soluble fibers are roasted and ground into a very fine paste by proprietary equipment. The paste may be packed as is, as a high nutritional base that can be used for thickening gravies, soups and preparation of many oriental and Indian type dishes such as meat or vegetarian satay, curries, hummus etc.

Additional usage can be to prepare dips such as tehini dip, prepared in conjunction with sesame paste or oil, water, garlic, lemon juice, spices and herbs. The tehini dip can be used as is or made into salad dressings, etc.

A sesame/coffee type roaster is used for roasting and controlled temperature heating of the *Salvia sclarea* seeds, which are then ground and homogenized into an omega-3 rich tehini-type paste.

Example 8: Production of Omega-3 Enriched Oil Preparations

*Salvia sclarea* whole seeds are washed and soaked in a water solution of salts, acid regulators, natural antioxidants, natural flavors and natural colors. Soaking times vary according to the desired formulations. The soaked seeds are thoroughly drained of excess solution.

The treated and drained seeds are blended with fish oils, and natural marine flavors omega-3 EPA and DHA fatty acids in desired ratios according to product recipe.

The finished product is packed in glass, plastic or metal packaging and processed to render shelf stable or chilled products with long shelf lives. These products are actually described as vegetarian caviar (fish roe) like products with high nutritional values that include all the nutritional factors of *Salvia sclarea* seeds, and in addition the full group of omega-3 fatty acids (ALA, DHA and EPA) from vegetable and marine sources.

In this embodiment, the *Salvia sclarea* whole seeds are treated by soaking using a multi-stage battery of variable speed mixers. The differential soaking solutions contain osmotic and acid regulations, and natural antioxidants, flavors and colors. Time and temperatures are controlled and the solutions treated seeds are dewatered by low-speed centrifuges. The seeds are blended as described, and then processed by pasteurization/sterilization (according to pH of product) to yield shelf stable products.

Example 9: Production of Fish Feed Formulations

*Salvia sclarea* seeds are milled and blended at various ratios into fish feed formulations.

This embodiment provides sweet water or salty water fish with the entire range of nutritional benefits of *Salvia sclarea* special oil rich in omega-3 alpha linolenic acid, omega-6 linoleic acid and oleic acid.

The fish formulations are then extruded into floating or sinking pellets according to the type of fish to be fed.

The raised fish will contain in their fillets a relatively higher concentration of omega-3 fatty acids, which in turn can be controlled by the concentration of ALA (C18:3) which is also a precursor for natural synthesis of DHA (C22:6) in animal, poultry and fish flesh.

These feed formulae contain all typical ingredients and added *Salvia*(x) meal containing high value proteins, minerals and omega-3 oils.

Example 10: Production of Packaged or Encapsulated Oil

*Salvia sclarea* seed oil rich in omega-3 ALA is extracted from seeds. The oil is blended with olive and other vegetable oils, rich in mono-unsaturated and omega-6 fatty acids and fortified with natural proprietary antioxidants that will further prevent the oil mixture from oxidation and also will provide beneficial antioxidants (such as Vitamin E, Vitamin C and others) to the user. When the *Salvia sclarea* seed oil is used alone, without mixing with other oils, the need for antioxidants is substantially eliminated because of the natural properties of this oil that make it very slow to rancidify. See Example 11.

The ratio of monounsaturated fatty acids to omega-3 fatty acid and omega-6 fatty acid is calculated to be 1 to ½ to ½, in order to maintain the recommended ratio of ⅓ monousaturated fatty acid, ⅓ polyunsaturated a fatty acid (with a ratio of 1 to 1 between omega-3 fatty acid and omega-6 fatty acid) and ⅓ saturated fatty acids of vegetable or animal origin (such as palm oil, coconut oil, butter, etc.). All fats and oils should be trans-free.

The total fats/oil per daily use is calculated to be 60 gr. or 75 gr. (i.e., 27% of diets with 2000 calorie/day or 2500 calorie/day respectively).

About 2-3 grams a day of fish oils containing 1000 mg. omega-3 DHA and EPA PUFA, are enclosed separately to the package, in order to supply daily the whole range of omega-3 PUFA: ALA, EPA and DHA.

The entire fatty acids/oils daily portion is packed in a 3 compartment package which will include in compartment 1 the fluid oils blend (to be used in salads, cooking, etc.), in compartment 2 a spreadable saturated fatty acids mix (to be used by spreading on crackers, bread slices, etc.) and in compartment 3, the omega-3 PUFA rich, fish oils (to be used with fish salads, dishes, etc., or any other food with a compatible flavor).

The fish oil may also be encapsulated.

Special oil blends including natural herbal and other antioxidants, and rich in omega-3 and oleic acids may be compounded to yield nutritionally recommended ratios of omega-6:omega-3, mono-unsaturated poly unsaturated and saturated fatty acids.

Example 11: Comparative Stability of *Salvia Sclarea* Oil

It has been discovered that the *Salvia sclarea* seed oil has a remarkable stability that far exceeds that of other known vegetable oils that are rich in omega-3 fatty acids, such as Chia (*Salvia hispanica*), flaxseed, hemp, and others.

To test the stability of *Salvia sclarea* seed oil against oxidation, the standard Rancimat test was conducted at various temperatures. This test is detailed in Sullivan and Carpenter, Methods of Analysis for nutrition labeling, AOAC International, Chapter 1, 1993. The results were as follows:

| | |
|---|---|
| Oil stability (105° C.), hr | 6.6 |
| Oil stability (120° C.), hr | 2.4 |
| Oil stability (130° C.), hr | 0.85 |

This may be compared to the stability reported for Chia oil, such as that reported in Ixtaina et al, "Oxidative Stability of Chia (*Salvia hispanica* L.) Seed Oil: Effect of Antioxidants and storage Conditions," *J Am Oil Chem Soc* 89:1077-1090 (2012). That article reports the induction time in hours as a result of the same Rancimat test used above for analyzing *S. sclarea* oil, but conducted at 98° C., as being 2.3±0.3. Thus, even at a much lower temperature (98° C.), the Chia oil became rancid faster than *S. sclarea* oil tested at 120° C. As the higher the temperature, the more rapid the oxidation, it is clear that *S. sclarea* oil is much more stable than is Chia oil. This significantly enhanced stability over Chia oil is surprising and unexpected.

Example 12: Assessment of Oxidative Deterioration of *Salvia Sclarea* Seed Oil at Ambient and Sunlight Storage This study was carried out in order to probe the extent of oxidative alterations in *Salvia sclarea* (Sage) seed oil, subjected to ambient and sunlight storage, over a period of different times and storage conditions. The results are shown in Tables 7-14.

The magnitude of oxidative changes was monitored by the periodic measurement of peroxide value (PV) (analysis Method—AOCS Cd 8b-90) and free fatty acid (FFA) content, (analysis Method—AOCS Ca 5a-40). A twelve month oil of cold press *Salvia sclarea* seeds was used from two different batches, with no addition of industrial or natural stabilizers to the oil. The protein in oil was <0.1%, moisture 0.04% max with an average 50% of ALA in the oil.

TABLE 7

Shelf life test 1: Glass bottle 250 cc of Sage Oil

| Batch number: | 11AE15 | 11AE15 | 11AE15 | 11AE15 | 11AE15 | 11AE15 | 11AE15 |
|---|---|---|---|---|---|---|---|
| Days at 40° C. acceleration | 0 | 30 | 60 | 90 | 120 | 150 | 180 |
| Free fatty acid content % as oleic acid (FFA) | 0.92 | 1.03 | 1.02 | 1.08 | 1.13 | 0.96 | 0.92 |
| peroxide value (PV) (meq/kg) | 7.4 | 5 | 3.7 | 6.5 | 3.3 | 3 | 7.6 |

TABLE 8

Shelf life test 2: Glass bottle 250 cc of Sage Oil

| Batch number: | 12AE16 | 12AE16 | 12AE16 | 12AE16 | 12AE16 | 12AE16 | 12AE16 |
|---|---|---|---|---|---|---|---|
| Days at 40° C. acceleration | 0 | 30 | 60 | 90 | 120 | 150 | 180 |
| Free fatty acid content % as oleic acid (FFA) | 1.11 | 1.18 | 1.21 | 1.3 | 1.35 | 1.37 | 1.08 |
| peroxide value (PV) (meq/kg) | 6.4 | 4.6 | 3.6 | 6.2 | 2.7 | 2.1 | 6.5 |

TABLE 9

Shelf life test 3: Glass bottle 250 cc of Sage Oil

| Batch number: | 11AE15 | 11AE15 | 11AE15 | 11AE15 | 11AE15 |
|---|---|---|---|---|---|
| Days at 25° C. | 0 | 90 | 123 | 270 | 365 |
| Free fatty acid content % as oleic acid (FFA) | 0.92 | 0.96 | 0.96 | 1.01 | 1.03 |
| peroxide value (PV) (meq/kg) | 7.4 | 6 | 4.9 | 3.3 | 3.6 |

TABLE 10

Shelf life test 4: Glass bottle 250 cc of Sage Oil

| Batch number: | 12AE16 | 12AE16 | 12AE16 | 12AE16 | 12AE16 |
|---|---|---|---|---|---|
| Days at 25° C. | 0 | 90 | 123 | 270 | 365 |
| Free fatty acid content % as oleic acid (FFA) | 1.11 | 1.2 | 1.13 | 1.25 | 1.22 |
| peroxide value (PV) (meq/kg) | 6.4 | 5.5 | 4.3 | 3 | 2.9 |

TABLE 11

Shelf life test 5: PET bottle 250 cc of Sage Oil

| Batch number: | 11AE15 | 11AE15 | 11AE15 | 11AE15 | 11AE15 |
|---|---|---|---|---|---|
| Days at −22° C. | 0 | 90 | 123 | 270 | 365 |
| Free fatty acid content % as oleic acid (FFA) | 0.92 | 0.94 | 0.95 | 0.91 | 0.97 |
| peroxide value (PV) (meq/kg) | 7.4 | 8.1 | 7.2 | 5.6 | 5.7 |

TABLE 12

Shelf life test 6: PET bottle 250 cc of Sage Oil

| Batch number: | 12AE16 | 12AE16 | 12AE16 | 12AE16 | 12AE16 |
|---|---|---|---|---|---|
| Days at −22° C. | 0 | 90 | 123 | 270 | 365 |
| Free fatty acid content % as oleic acid (FFA) | 0.92 | 1.16 | 1.09 | 0.88 | 1.03 |
| peroxide value (PV) (meq/kg) | 7.4 | 6.7 | 6.6 | 11.7 | 5.4 |

TABLE 13

Shelf life test 7: Glass bottle 250 cc of Sage Oil

| Batch number: | 11AE15 | 11AE15 | 11AE15 |
|---|---|---|---|
| Days at 4° C. | 0 | 180 | 365 |
| Free fatty acid content % as oleic acid (FFA) | 0.92 | 0.94 | 0.96 |
| peroxide value (PV) (meq/kg) | 7.4 | 7.6 | 5.3 |

TABLE 14

Shelf life test 8: Glass bottle 250 cc of Sage Oil

| Batch number: | 12AE16 | 12AE16 | 12AE16 |
|---|---|---|---|
| Days at 4° C. | 0 | 180 | 365 |
| Free fatty acid content % as oleic acid (FFA) | 1.11 | 1.08 | 1.13 |
| peroxide value (PV) (meq/kg) | 6.4 | 6.5 | 4.7 |

These results may be contrasted to the PV values for flax seed oil, such as those reported in Hamed and Abo-Elwafa, "Enhancement of oxidation stability of flax seed oil by blending with stable vegetable oils," *J App Sci Res* 8:5039-5048 (2012). This publication reports that relatively short shelf-life of most commercially available vegetable oils limits their usefulness in various applications. It further states that flax seed oil, with the high levels of PUFA, is more readily oxidized if stored or handled improperly. While accelerated at 62° C., the PV values for pure flax seed oil (FO) in FIG. 4, are extremely high as compared to the results above for *S. sclarea* seed oil.

See also the peroxide value (PV) for Chia oil as reported in FIG. 4 of Ixtaina (2012), supra. It shows that fresh Chia oil at 20° C. after 195 days has a PV of 20. This may be compared with one year *Salvia sclarea* oil at 25° C. after 270 days, which has a PV of only 3.3 and one year *Salvia sclarea* oil at 40° C. after 365 days, which has a PV of only 3.6.

The extremely high stability of *S. sclarea* seed oil, as compared to other oils high in omega-3, is surprising and unexpected.

The invention claimed is:

1. A supplemented food product, comprising a food product other than *Salvia sclarea* seed, *Salvia sclarea* seed oil, extracts from *Salvia sclarea* seeds, and *Salvia sclarea* seed crushed or milled to form a flour or powder, to which has been added *Salvia sclarea* seed, *Salvia sclarea* seed oil, extracts from *Salvia sclarea* seeds, or *Salvia sclarea* seed crushed or milled to form a flour or powder, wherein said food product is selected from the group consisting of granola cereal, granola snack bar, foodstuff for hens, foodstuff for cattle, foodstuff for fish, pasta, baked goods, a thickener, gravy, soup, a dip, dressing, prepared food that contains flour as a thickener, tahini, humus, sesame seed, sesame oil, sesame paste, margarine, margarine spread, salad dressing, dairy products, yeast, fish oil, caviar product and a shake.

2. A supplemented food product in accordance with claim 1, wherein said food product is granola cereal or granola snack bar.

3. A supplemented food product in accordance with claim 1, wherein said food product is foodstuff for hens.

4. A supplemented food product in accordance with claim 1, wherein said food product is foodstuff for cattle.

5. A supplemented food product in accordance with claim 1, wherein said food product is foodstuff for fish.

6. A supplemented food product in accordance with claim 1, wherein said food product is bread, a roll, a cracker, a biscuit, or another baked good.

7. A supplemented food product in accordance with claim 1, wherein said food product is pasta.

8. A supplemented food product in accordance with claim 1, wherein said food product is a thickener or a prepared food that contains flour as a thickener.

9. A supplemented food product in accordance with claim 1, wherein said food product is gravy.

10. A supplemented food product in accordance with claim 1, wherein said food product is soup.

11. A supplemented food product in accordance with claim 1, wherein said food product is a dip.

12. A supplemented food product in accordance with claim 1, wherein said food product is a dressing or a salad dressing.

13. A supplemented food product in accordance with claim 1, wherein said food product is tahini, sesame seed, sesame oil, or sesame paste.

14. A supplemented food product in accordance with claim 1, wherein said food product is humus.

15. A supplemented food product in accordance with claim 1, wherein said food product is margarine or margarine spread.

16. A supplemented food product in accordance with claim 1, wherein said food product is a caviar product.

17. A supplemented food product in accordance with claim 1, wherein said food product is a dairy product.

18. A supplemented food product in accordance with claim 1, wherein said food product is yeast.

19. A supplemented food product in accordance with claim 1, wherein said food product is fish oil.

20. A supplemented food product in accordance with claim 1, wherein said food product is a shake.

* * * * *